(12) United States Patent
Yuki et al.

(10) Patent No.: US 12,280,098 B2
(45) Date of Patent: Apr. 22, 2025

(54) PNEUMOCOCCAL SURFACE PROTEINS

(71) Applicants: The University of Tokyo, Tokyo (JP); HanaVax Inc., Tokyo (JP)

(72) Inventors: Yoshikazu Yuki, Tokyo (JP); Rika Nakahashi, Tokyo (JP); Hiroshi Kiyono, Tokyo (JP)

(73) Assignees: THE UNIVERSITY OF TOKYO, Tokyo (JP); HANAVAX INC., Tokyo (JP)

( * ) Notice: Subject to any disclaimer, the term of this patent is extended or adjusted under 35 U.S.C. 154(b) by 765 days.

(21) Appl. No.: 17/599,101

(22) PCT Filed: Mar. 27, 2020

(86) PCT No.: PCT/JP2020/013929
§ 371 (c)(1),
(2) Date: Sep. 28, 2021

(87) PCT Pub. No.: WO2020/203731
PCT Pub. Date: Oct. 8, 2020

(65) Prior Publication Data
US 2022/0160860 A1 May 26, 2022

(30) Foreign Application Priority Data
Mar. 29, 2019 (JP) .................. 2019-065362

(51) Int. Cl.
A61K 39/09 (2006.01)
A61P 31/04 (2006.01)
C07K 14/315 (2006.01)

(52) U.S. Cl.
CPC ............ A61K 39/092 (2013.01); A61P 31/04 (2018.01); C07K 14/3156 (2013.01)

(58) Field of Classification Search
None
See application file for complete search history.

(56) References Cited

U.S. PATENT DOCUMENTS

| | | | |
|---|---|---|---|
| 5,965,400 A * | 10/1999 | Briles ................ | C07K 14/7151 435/69.3 |
| 11,806,392 B2 * | 11/2023 | Briles .................. | A61K 39/092 |
| 2015/0320851 A1 | 11/2015 | Akeda et al. | |
| 2017/0014338 A1 | 1/2017 | Yuki et al. | |
| 2018/0214530 A1 | 8/2018 | Kong et al. | |

FOREIGN PATENT DOCUMENTS

| | | |
|---|---|---|
| JP | 2015-151375 | 8/2015 |
| WO | 2014/045621 | 3/2014 |
| WO | 2018/102774 | 6/2018 |

OTHER PUBLICATIONS

S Noguchi—Nihon Kessho Gakkaishi, 1998—jstage.jst.go.jp vol. 40, pp. 272-278 (Year: 1998).*

McDaniel et al., (1994 Microb. Pathogen. 17 (5), 323-337). (Year: 1994).*

Office Action issued Apr. 9, 2024 in Japanese patent application No. 2021-511975, with English translation thereof.

Office Action issued Jun. 8, 2024 in Chinese patent application No. 202080025656.2, with English translation thereof.

Office Action dated Sep. 30, 2023 issued in Saudi Arabian patent application No. 521430442, with English translation thereof.

Extended European Search Report issued Nov. 30, 2022 in corresponding European Patent Application No. 20783992.9.

Charles Feldman et al., "Review: Current and new generation pneumococcal vaccines", Journal of Infection, vol. 69, pp. 309-325, 2014.

Notification of the Substantive Examination Report issued Nov. 7, 2022 in corresponding Saudi Arabian Patent Application No. 521430442, with English language translation.

Noguchi, Shuji, "Isomerization of Aspartic Acid in Protein", 1998, vol. 40, pp. 272-278. Cited in ISR.

Berry, A. M. et al., "Reduced Virulence of a Defined Pneumolysin-Negative Mutant of *Streptococcus pneumoniae*", Infection and Immunity, Jul. 1989, vol. 57, No. 7, pp. 2037-2042.

McDaniel, L. S. et al., "Use of Insertional Inactivation To Facilitate Studies of Biological Properties of Pneumococcal Surface Protein A (PspA)", J. Exp. Med., Feb. 1987, vol. 165, pp. 381-394.

Briles, D. E. et al., "Intranasal Immunization of Mice with a Mixture of the Pneumococcal Proteins PsaA and PspA Is Highly Protective against Nasopharyngeal Carriage of *Streptococcus pneumoniae*", Infection and Immunity, Feb. 2000, vol. 68, No. 2, pp. 796-800.

Nguyen, C. T. et al., "Intranasal immunization with recombinant PspA fused with a flagellin enhances cross-protective immunity against *Streptococcus pneumoniae* infection in mice", Vaccine, 2011, vol. 29, pp. 5731-5739.

McCool, T. L. et al., "The Immune Response to Pneumococcal Proteins during Experimental Human Carriage", J. Exp. Med., Feb. 2002, vol. 195, pp. 359-365.

(Continued)

*Primary Examiner* — Jana A Hines
*Assistant Examiner* — Khatol S Shahnan Shah
(74) *Attorney, Agent, or Firm* — GREENBLUM & BERNSTEIN, P.L.C.

(57) ABSTRACT

The present invention provides D39-derived mutant PspA that does not undergo deamination and maintains stability as a molecule even around neutral pH range.

Specifically, the present invention relates to a protein of the following (a) or (b):

(a) a protein comprising the amino acid sequence as set forth in SEQ ID NO: 2 and having pneumococcal vaccine antigenic activity, and a protein substantially identical to the protein; or (b) a protein being a part of the amino acid sequence as set forth in SEQ ID NO: 2, wherein aspartic acid at position 254 is comprised in the part, and having pneumococcal vaccine antigenic activity, and a protein substantially identical to the protein.

9 Claims, 2 Drawing Sheets
Specification includes a Sequence Listing.

(56) References Cited

OTHER PUBLICATIONS

Office Action dated Aug. 18, 2023, issued in Russian patent application No. 2021130034/10(063656), with English translation thereof.
Añez et al., "Passage of Dengue Virus Type 4 Vaccine Candidates in Fetal Rhesus Lung Cells Selects Heparin-Sensitive Variants That Result in Loss of Infectivity and Immunogenicity in Rhesus Macaques," *Journal of Virology*, vol. 83, No. 20, Oct. 2009, pp. 10384-10394.
Office Action dated Jul. 23, 2023, issued in Chinese patent application No. 202080025656.2, with English translation thereof.
Office Action dated Sep. 30, 2024, issued in European patent application No. 20783992.9.

\* cited by examiner

PNEUMOCOCCAL SURFACE PROTEINS

The present application is a national stage entry of International application no. PCT/JP2020/013929, filed Mar. 27, 2020, which claims priority to Japanese patent application no. 2019-065362, filed Mar. 29, 2019.

TECHNICAL FIELD

The present invention relates to a pneumococcal surface protein A (PspA) and a vaccine comprising the PspA.

BACKGROUND ART

Pneumococcus, as well as influenza virus, is a clinically important upper respiratory tract infection pathogen, and is associated with otitis media, pneumonia, bacteremia, meningitis, and the like. Pneumococcus causes severe diseases including death to both children and adults.

In recent years, as a means for protecting against infection caused by such pneumococcus, 7-valent, 10-valent- and 13-valent polysaccharide pneumococcal conjugate vaccines (PCV7, PCV10, and PCV13) have been developed for adults, and have been administered to patients via intramuscular injection. However, since T cell-independent polysaccharide in these polysaccharide-based vaccines has low immunogenicity, the polysaccharide-based vaccines hardly induce immune response to children, and exhibit protective effects only against capsular serotype pneumococci. Moreover, it is problematic that since the vaccines administered via intramuscular injection mainly induce systemic anti-IgG antibodies, these vaccines cannot induce mucosal immune response to pneumococci.

A pneumococcal surface protein A (PspA) existing on the surface layer of pneumococcus has been known as a protein having high immunogenicity, and has been considered to be promising as a candidate of vaccines (Non Patent Literature 1 and Non Patent Literature 2). PspA is present on almost all types of pneumococci, and PspA-based vaccines induce antibodies provoking cross-reactions in mice and humans (Non Patent Literature 3 to Non Patent Literature 5). In addition, PspA-specific mucosal and systemic antibodies are induced to baby mice (through the mother's body) and adult mice, and this antibody induction is mediated by the Th1 and Th2 cytokine response of $CD4^+$ T cells. The aforementioned findings suggest that PspA may be a pneumococcal vaccine candidate effective not only for adults, but also for children.

PspA is classified into three families (i.e., Families 1 to 3), and is further classified into six subgroups called "clades" (i.e., Clades 1 to 6). Among these, a pneumococcal strain having PspA classified into Family 1 accounts for approximately 95% of the previously confirmed strains, and the PspA classified into Family 1 is particularly important as a vaccine candidate.

D39 strain-derived PspA known as a universal antigen of pneumococcus is a representative vaccine antigen classified into Family 1, Clade 2. The D39 strain-derived PspA has high antigenicity and a high ability to induce a pneumococcus neutralizing antibody. However, the D39 strain-derived PspA has been easily deaminated around neutral pH range, and has been problematic in terms of safety.

CITATION LIST

Non Patent Literature

Non Patent Literature 1: Berry et al., Infect Immun 57: 2037-2042, 1989

Non Patent Literature 2: McDaniel et al., J Exp Med 165: 381-394, 1987

Non Patent Literature 3: Briles et al., Infect Immun 68: 796-800, 2000

Non Patent Literature 4: Nguyen et al., Vaccine 29: 5731-5739, 2011

Non Patent Literature 5: McCool et al., J Exp Med 195: 359-365, 2002

SUMMARY OF INVENTION

Technical Problem

Considering the aforementioned circumstances, it is an object of the present invention to provide a D39-derived mutant PspA that does not undergo deamination and maintains stability as a molecule even around neutral pH range.

Solution to Problem

The present inventors have analyzed the amino acid sequences of a deaminated D39-derived PspA according to an MS/MS method. As a result, the inventors have discovered that a mutation is generated in one amino acid of a wild-type D39-derived PspA.

With regard to this amino acid position, it has been clarified that only the asparagine (Asn) at position 254 is specifically changed to aspartic acid (Asp) in the entire amino acid sequence of the wild-type D39-derived mature PspA as set forth in SEQ ID NO: 1. PspA (N254D), in which the position 254 of the D39-derived mature PspA is changed to aspartic acid, is extremely stable, and its antigenicity and ability to induce a neutralizing antibody are not changed. Moreover, such a change in the amino acid has not been found, for example, in the PspA of the pneumococcal strain EF3296 belonging to Family 2, Clade 3, or in the PspA of the pneumococcal strain EF5668 belonging to Family 2, Clade 4.

Based on the aforementioned findings, the present invention has been completed.

Specifically, the present invention includes the following (1) to (5).

(1) A protein of the following (a) or (b):
  (a) a protein comprising the amino acid sequence as set forth in SEQ ID NO: 2 and having pneumococcal vaccine antigenic activity, and a protein substantially identical to the protein; or
  (b) a protein being a part of the amino acid sequence as set forth in SEQ ID NO: 2, wherein aspartic acid at position 254 is comprised in the part, and having pneumococcal vaccine antigenic activity, and a protein substantially identical to the protein.

(2) The protein according to the above (1), wherein the part of the amino acid sequence as set forth in SEQ ID NO: 2 is characterized by being an α-helix region.

(3) The protein according to the above (2), wherein the protein is characterized by being the whole or a part of the amino acid sequence as set forth in SEQ ID NO: 3.

(4) DNA encoding the protein according to any one of the above (1) to (3).

(5) A pneumococcal vaccine comprising the protein according to any one of the above (1) to (3) as an antigen or a part of the antigen.

Advantageous Effects of Invention

According to the present invention, a pneumococcal vaccine antigen stable as a molecule is provided. Specifically, in a purification process in an ion exchange chromatography, etc. performed in the production of a conventional, pharmaceutical-grade D39 pneumococcus-derived PspA, an elution peak has been divided into two portions in some cases, and a latter peak has been a deamination form. The antigen provided by the present invention can show that a preparation that is extremely stable in a purification process and the subsequent preservation state can be prepared.

DESCRIPTION OF EMBODIMENTS

The present invention provides a protein that maintains antigenicity and an ability to induce a neutralizing antibody that are equivalent to those of a wild-type D39-derived PspA protein, and is more excellent than such a wild-type D39-derived PspA protein in terms of stability as a molecule (for example, unlikeliness of an amino acid mutation, etc.) (hereinafter referred to as "the PspA protein of the present invention").

That is to say, a first embodiment of the present invention relates to the PspA protein of the present invention that is a protein of the following (a) or (b):
  (a) a protein comprising the amino acid sequence as set forth in SEQ ID NO: 2 and having pneumococcal vaccine antigenic activity, and a protein substantially identical to the protein; or
  (b) a protein being a part of the amino acid sequence as set forth in SEQ ID NO: 2, wherein aspartic acid at position 254 is comprised in the part, and having pneumococcal vaccine antigenic activity, and a protein substantially identical to the protein.

Figure 1:
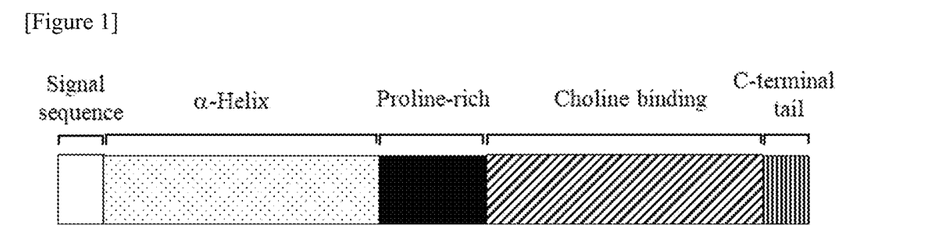
FIG. 1 is a view schematically showing the structure of a PspA protein.

The present PspA protein is composed of a signal sequence (e.g., the amino acid positions 1 to 31 of GenBank accession no.: ABJ54172 (derived from the D39 strain)), an α-helix region (e.g., the amino acid positions 32 to 319 of GenBank accession no.: ABJ54172), a proline-rich region (e.g., the amino acid positions 320 to 402 of GenBank accession no.: ABJ54172), a choline binding region, and a C-terminal tail region, from the N-terminal side thereof (see FIG. 1). The signal sequence is cleaved to become a mature PspA (which is composed of an α-helix region, a proline-rich region, a choline binding region, and a C-terminal tail region).

In the embodiment of the present invention, the "pneumococcal vaccine antigenic activity" means the activity of inducing immunity (humoral immunity and/or cell-mediated immunity) for protecting a living body from attack by pneumococcus. Whether or not a certain protein has "pneumococcal vaccine antigenic activity" can be easily confirmed by a person skilled in the art (for example, it can be confirmed by the method described in "4. Transnasal immunization to mice" in Examples).

The term "the protein" used in the above (a) means "a protein comprising the amino acid sequence as set forth in SEQ ID NO: 2 and having pneumococcal vaccine antigenic activity," whereas the term "the protein" used in the above (b) means "a protein being a part of the amino acid sequence as set forth in SEQ ID NO: 2, wherein aspartic acid at position 254 is comprised in the part, and having pneumococcal vaccine antigenic activity."

In the embodiment of the present invention, the phrase "a protein substantially identical to the protein" means a protein consisting of an amino acid sequence comprising a deletion (excluding the aspartic acid at position 254), a substitution (excluding the aspartic acid at position 254), an insertion, or an addition of one or several amino acids (preferably about 1 to 30, more preferably about 1 to 10, and further preferably 1 to 5 amino acids) in the amino acid sequence of "the protein" as described above, wherein "the protein" has activity as a pneumococcal vaccine antigen.

Otherwise, in the embodiment of the present invention, the phrase "a protein substantially identical to the protein" means a protein comprising an amino acid sequence having an amino acid identity of approximately 60% or more, preferably approximately 70% or more, more preferably approximately 80%, 81%, 82%, 83%, 84%, 85%, 86%, 87%, 88%, 89%, 90%, 91%, 92%, 93%, 94%, 95%, 96%, 97%, or 98%, and most preferably approximately 99%, to the amino acid sequence of "the protein" as described above, wherein the amino acid at position 254 is aspartic acid, and "the protein" has activity as a pneumococcal vaccine antigen.

The phrase "a part of the amino acid sequence as set forth in SEQ ID NO: 2" used in the above (b) preferably means a region comprising, for example, a part of or the whole of an α-helix region (comprising the aspartic acid at position 254) and a part of or the whole of a proline-rich region, and it may be, for example, a protein consisting of the amino acids as set forth in SEQ ID NO: 3.

A second embodiment of the present invention relates to a nucleic acid (DNA, etc.) encoding "the PspA protein of the present invention." The PspA protein of the present invention can be prepared by obtaining a nucleic acid encoding itself from a cDNA library or the like, incorporating the nucleic acid into a suitable expression vector, transforming or transfecting suitable host cells with the expression vector, and then culturing the host cells in a suitable medium, so that the cells are allowed to express the PspA protein of the present invention, which is then purified.

Examples of the host cells that can be used herein for the expression of the PspA protein may include bacterial cells (e.g., *Escherichia coli* B strain, *E. coli* K12 strain, *Corynebacterium ammoniagenes*, *C. glutamicum*, *Serratia liquefaciens*, *Streptomyces lividans*, *Pseudomonas putida*, etc.), molds (e.g., *Penicillium camembertii*, *Acremonium chrysogenum*, etc.), animal cells, plant cells, baculovirus/insect cells, and yeast cells (e.g., *Saccharomyces cerevisiae* and *Pichia pastoris*, etc.). The PspA protein can be expressed in these cells.

As an expression vector for expressing the PspA protein, a vector suitable for various types of host cells can be used. Examples of such an expression vector that can be used herein may include: pBR322, pBR325, pUC118, or pET (*Escherichia coli* hosts); pEGF-C and pEGF-N (animal cell hosts); pVL1392 and pVL1393 (insect cell hosts, baculovirus vectors); and pG-1, Yep13, or pPICZ (yeast cell hosts).

These expression vectors have a replication origin, a selective marker and a promoter, which are suitable for individual vectors, and may also have, as necessary, an enhancer, a transcription terminator sequence (terminator), a ribosome binding site, a polyadenylation signal, and the like. Moreover, in order to facilitate the purification of the expressed polypeptide, a nucleotide sequence for fusing a FLAG tag, a His tag, an HA tag, a GST tag and the like and expressing them may be inserted into the expression vector.

Such an expression vector can be produced by a method known to a person skilled in the art, and a commercially available kit and the like can be used, as appropriate.

When the expressed PspA protein is extracted from a cultured cell mass or cultured cells, such a cell mass or cultured cells are collected by a known method after completion of the culture, and the cell mass or the cultured cells are then suspended in a suitable buffer solution. Thereafter, the cell mass or the cultured cells are destructed, for example, by ultrasound, lysozyme, and/or freezing-thawing, and thereafter, a soluble extract is obtained by centrifugation or filtration. In particular, when the cultured cells are used as hosts, a method of obtaining a PspA protein expressed in a culture supernatant by recovering the supernatant is desirably applied. A protein of interest can be obtained from the obtained extract or culture supernatant by appropriately combining known separation/purification methods with one another. Examples of the known separation/purification methods may include: methods of utilizing solubility, such as salting-out and a solvent precipitation method; methods of mainly utilizing a difference in molecular weight, such as a dialysis method, an ultrafiltration method, a gel filtration method, and SDS-PAGE; methods of utilizing a difference in electric charge, such as ion exchange chromatography; methods of utilizing specific affinity, such as affinity chromatography (for example, a resin, in which glutathione is allowed to bind to a carrier, is used in a case where a polypeptide is allowed to express together with a GST tag; a Ni-NTA resin or a Co-based resin is used in a case where a polypeptide is allowed to express together with a His tag; an anti-HA antibody resin is used in a case where a polypeptide is allowed to express together with an HA tag; and an anti-FLAG antibody-binding resin or the like is used in a case where a polypeptide is allowed to express together with a FLAG tag); methods of utilizing a difference in hydrophobicity, such as reversed phase high-performance liquid chromatography; and methods of utilizing a difference in isoelectric point, such as an isoelectric focusing method.

A third embodiment of the present invention relates to a vaccine for suppressing infection caused by pneumococci, comprising the PspA protein of the present invention as an antigen (hereinafter also referred as "the pneumococcal vaccine of the present invention").

The PspA protein of the present invention comprised in the pneumococcal vaccine of the present invention may be comprised alone. However, the present PspA protein may also be comprised in the present pneumococcal vaccine in the form of being fused with the whole or a part of a PspA protein different from the PspA protein of the present invention (including a PspA protein belonging to a different family and/or a different clade) (see, for example, WO2018102774, etc.).

The pneumococcal vaccine of the present invention may comprise one or several types of adjuvants, such as, for example, a complete Freund's adjuvant or an incomplete Freund's adjuvant, cholera toxin, heat-labile E. coli toxin, aluminum hydroxide, potassium alum, saponin or a derivative thereof, muramyl dipeptide, mineral oil or vegetable oil, Novasome or a nonionic block copolymer, and DEAE dextran. Moreover, the pneumococcal vaccine of the present invention may also comprise a pharmaceutically acceptable carrier. Such a pharmaceutically acceptable carrier needs to be a compound that does not affect the health of an animal to be vaccinated. The pharmaceutically acceptable carrier is, for example, sterilized water or a buffer.

The pneumococcal vaccine of the present invention can be administered according to an ordinary active immunization method. The present pneumococcal vaccine may be administered either by injection, or by a transmucosal method, such as oral or transnasal administration. Moreover, the pneumococcal vaccine can be administered once or multiple times, in an amount effective for the prevention or treatment of pneumococcal infection (i.e., in an amount sufficient for inducing immunity to the attack by pneumococci in a living body), according to a method suitable for a dosage form. The pneumococcal vaccine can be administered via intradermal, subcutaneous, intramuscular, intraperitoneal, intravenous, oral or transmucosal (intranasal or sublingual administration, etc.) administration. Furthermore, the pneumococcal vaccine of the present invention can also be used by being mixed with other antigenic components.

The dose and the number of doses of the present pneumococcal vaccine may be changed depending on the administration subject. The pneumococcal vaccine comprising several tens μg of antigen is administered to a subject several times at a frequency of once a week to once several weeks, so that it can induce defensive immunity to the subject.

Further, the pneumococcal vaccine of the present invention may comprise a nanogel, such that it becomes suitable for transnasal administration. In the embodiment of the present invention, the term "nanogel" is used to mean polymeric gel nanoparticles, in which a hydrophobic cholesterol is added as a side chain to a hydrophilic polysaccharide (e.g., pullulan). Such a nanogel can be produced according to a known method, such as the method described, for example, in International Publication WO2000/012564.

Specifically, first, a hydroxyl group-containing hydrocarbon having 12 to 50 carbon atoms or a sterol is allowed to react with a diisocyanate compound represented by OCN—$R_1$ NCO (wherein $R_1$ represents a hydrocarbon group having 1 to 50 carbon atoms) to produce an isocyanate group-containing hydrophobic compound, with which a single molecule of the hydroxyl group-containing hydrocarbon having 12 to 50 carbon atoms or sterol is reacted. The obtained isocyanate group-containing hydrophobic compound is allowed to react with a polysaccharide to produce a hydrophobic group-containing polysaccharide comprising a hydrocarbon group having 12 to 50 carbon atoms or a steryl group. Subsequently, the obtained product is purified in a ketone-based solvent to produce a hydrophobic group-containing polysaccharide with a high purity.

As a polysaccharide used herein, pullulan, amylopectin, amylose, dextran, hydroxyethyl dextran, mannan, levan, inulin, chitin, chitosan, xyloglucan, water-soluble cellulose, etc. can be utilized, and pullulan is particularly preferable.

Examples of the nanogel used in the third embodiment of the present invention may include cationic cholesteryl-group-bearing pullulan (referred to as "cCHP") and a derivative thereof. The cCHP has a structure, in which 1 to 10 cholesterols, preferably, one to several cholesterols are substituted per 100 monosaccharides in pullulan having a molecular weight of 30,000 to 200,000, for example, having a molecular weight of 100,000. Besides, the cCHP used in the present invention may be changed, as appropriate, in terms of the amount of cholesterols substituted, depending on the size of an antigen or the degree of hydrophobicity. In addition, in order to change the degree of hydrophobicity of the CHP, an alkyl group (having approximately 10 to 30, preferably approximately 12 to 20 carbon atoms) may be added to the CHP. The nanogel used in the present invention has a particle diameter of 10 to 40 nm, and preferably of 20 to 30 nm. The nanogels have already been widely marketed, and such commercially available nanogel products may also be used.

The nanogel used in the embodiment of the present invention is a nanogel into which a functional group having a positive charge, such as, for example, an amino group, is introduced, so that a vaccine can invade in the surface of the negatively charged nasal mucosa. As a method of introducing an amino group into a nanogel, a method of using an amino group-added cholesterol pullulan ($CHPNH_2$) can be applied. Specifically, CHP dried under reduced pressure is dissolved in dimethyl sulfoxide (DMSO), and 1,1'-carbonyldiimidazole is then added to the obtained solution under a nitrogen air current, followed by performing a reaction at room temperature for several hours. Thereafter, ethylenediamine is gradually added to the reaction solution, and the obtained mixture is then stirred for several hours to several tens of hours. The obtained reaction solution is dialyzed against distilled water for several days. After completion of the dialysis, the reaction solution is freeze-dried to obtain an opalescent solid. The substitution degree of ethylenediamine can be evaluated using elemental analysis, H-NMR, etc.

The pneumococcal vaccine of the present invention may comprise pharmaceutically acceptable, known stabilizers, antiseptics, antioxidants, etc. The stabilizers may include gelatin, dextran, and sorbitol. The antiseptics may include thimerosal and β propiolactone. The antioxidant may be a tocopherol.

A fourth embodiment of the present invention relates to a method for preventing infectious diseases caused by pneumococci, comprising administering the pneumococcal vaccine of the present invention to a patient.

Herein, the term "prevent" means that, in a patient who may be infected with pneumococcus, the infection is previously prevented, and thereby, prevention is a treatment for the purpose of previously preventing the onset of pneumococcal infection.

The disclosures of all publications cited in the present description are incorporated herein by reference in their entireties. In addition, when an English translation of the present description includes singular terms with the articles "a," "an," and "the," these terms include not only single items but also multiple items, unless otherwise clearly specified from the context.

Hereinafter, the present invention will be further described in the following examples. However, these examples are only illustrative examples of the embodiments of the present invention, and thus, are not intended to limit the scope of the present invention.

EXAMPLES

1. Native PAGE

An *Escherichia coli* expression system, etc. was allowed to express various types of PspA proteins, namely, PspA 1-1 (SEQ ID NO: 5), PspA 1-2 (SEQ ID NO: 6), PspA 1-3 (SEQ ID NO: 4), and PspA 1-3 LB (SEQ ID NO: 3) (see WO2018102774 for details). The expressed PspA proteins were extracted according to a common non-denaturing method, and were then purified according to LDS (Lithium Dodecyl Sulfate)-PAGE, using ion exchange chromatography, butyl sepharose and the like, until they became homogeneous.

First, the PspA 1-3 molecules were suspended in 2 mg/ml PBS immediately after the purification, and were then adjusted to predetermined pH values (pH 6.5, pH 7.0, pH 7.5, pH 8.0, and pH 8.5) with 0.5 M $NaH_2PO_4$ or 0.5 M $Na_2HP_4$, followed by preservation at 25° C. for a predetermined period of time (for 1 day, 2 days, and 5 days). Using 10 μl (1.0 μg/lane) of each sample, electrophoresis was carried out by using Native PAGE at 200 V for 60 minutes, and thereafter, Coomassie Blue (BioRad) staining was carried out. Besides, the gel used herein was 7.5% Mini-Protein TGX Gel 12 well (BioRad), the treatment solution used herein was Native Sample Buffer for Protein Gels (BioRad), and the electrophoresis buffer used herein was 10× Premixed electrophoresis buffer (BioRad).

Figure 2:
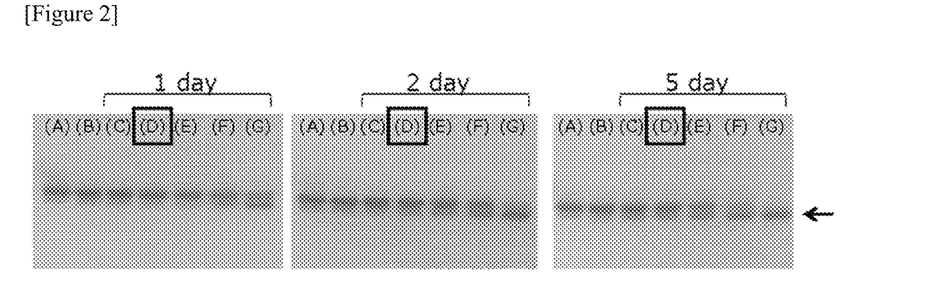
FIG. 2 shows the results obtained by confirming a molecular change in PspA 1-3 over time at the predetermined pH values (pH 6.5, pH 7.0, pH 7.5, pH 8.0, and pH 8.5) according to Native-PAGE. A: marker (500 mg); B: pH 7.0 (control on Day 0); C: pH 6.5; D: pH 7.0; E: pH 7.5; F: pH 8.0; and G:pH 8.5.

By performing a treatment under these conditions, in LDS-PAGE, all of the specimens exhibited a single band and the apparent molecular weight was not changed (no data shown), whereas in Native-PAGE, a band with high mobility was generated 5 days after completion of the treatment, regardless of pH (the arrow in FIG. 2). The protein corresponding to this band was defined to be PspA 1-3 LB. Although no data are shown, this phenomenon was observed in PspA 1-1 and PspA 1-2 immediately after the purification. On the other hand, this phenomenon was not observed in PspA 2 (derived from the strain EF3296) and PspA 3 (derived from the strain EF5668). Thus, it was considered that this phenomenon specifically occurs in the pneumococcus D39 strain-derived PspA.

2. Peptide Map

In order to specify a molecular change from PspA 1-3 to PspA 1-3 LB, 10 μg of trypsin (Sigma, sequence grade) was added to PspA 1-3 and PspA 1-3 LB (each 0.5 mg/ml) immediately after the purification, so that a digestion treatment was carried out at 37° C. for 24 hours at pH 8.5, and thereafter, 50 μl of the treated sample was introduced into reversed phase HPLC (Waters C18, 1.7 win, 2.1×100 mm). Thus, analysis was performed at a separation temperature of 50° C., by 110 min Linear-Gradient elution of 0.1% TFA (100%) and 0.1% TFA—40% acetonitrile (55%), at 0.2 ml/min, and at 220 nm (Detection).

Figure 3:
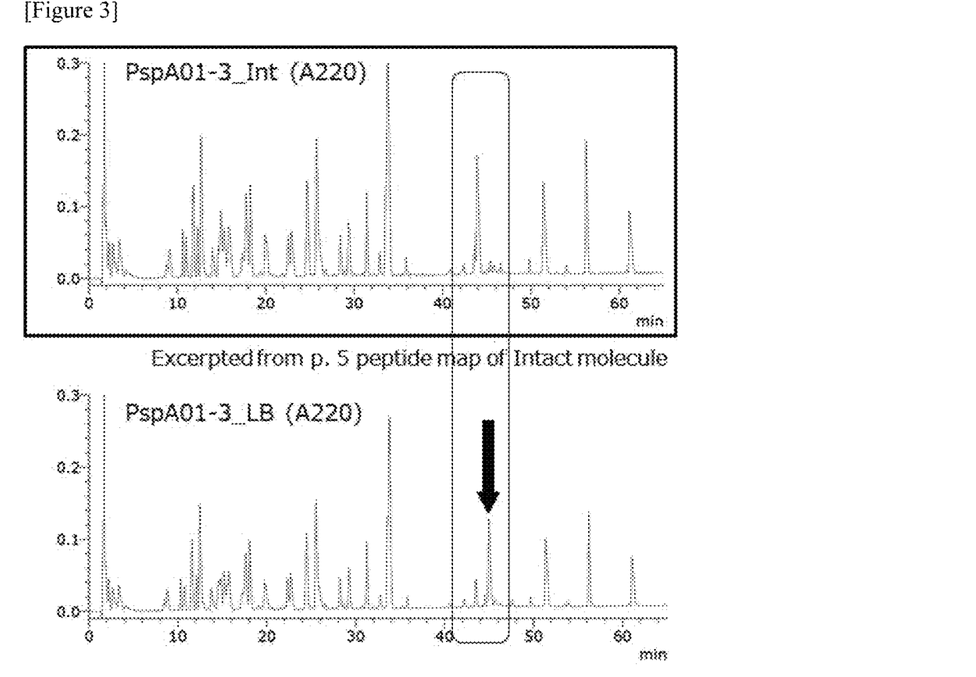
FIG. 3 shows the results of an analysis using peptide maps of PspA 1-3 and PspA 1-3 LB. The arrow indicates a peak specifically generated in PspA 1-3 LB.

As a result, a peak with a different elution time was detected (FIG. 3). Hence, the present peak was fractionated, and was then subjected to N-terminal analysis using a PPSQ-21A Protein sequencer (Shimadzu). As a result, a sequence of AAEENDNVE (SEQ ID NO: 7) was observed in PspA 1-3 LB. These results suggested that specific deamination would be likely to occur in the amino acid sequence of PspA 1-3 LB.

3. Determination of Amino Acid Sequence of PspA 1-3 LB

Subsequently, to analyze the entire amino acid sequence of PspA 1-3 LB, the same trypsin digestion as that described in the above 2. was carried out, and then, sequence analysis was carried out using LC-MS/MS (HPLC acquity UPLC (Waters: C4, 1.7 μm, 2.1×100 mm)—MS: Orbitrap Fusion Tribrid (Thermo) MS1: Orbitrap, MS2: Ion Trap.

As a result, a sequence of 208 amino acid residues (69%) was identified in 302 amino acid residues, and whole-MS analysis was also carried out (Intact form: 33569.03, and one deamination form: 33569.93). Since the obtained values were consistent with individual theoretical values, it was concluded that the possibility of occurrence of deamination other than N254D was extremely low.

4. Transnasal Immunization of Mice

4-1. Method

4-1-1. Formation of Nanogel Comprising Antigen (Preparation of Vaccine)

A cCHP nanogel and each PspA protein (PspA 1-1, PspA 1-2, PspA 1-3, and PspA 1-3 LB) were mixed with each other at a molecular ratio of 1:1, and the obtained mixture was then incubated using a heat block at 40° C. for 1 hour.

4-1-2. Transnasal Immunization of Mice

Each cCHP-PspA solution was transnasally administered to 7-week-old female Balb/c mice. With regard to the single dose of the antigen administered per mouse, 10 μg of the antigen was administered to each mouse, in terms of the amount of each PspA protein. Such transnasal immunization was carried out a total of three times with intervals of 1 week.

4-1-3. Preparation of Serum Samples from Immunized Mice

In order to measure PspA-specific IgG in serum, which increased 1 week after the final immunization, blood was collected from the orbital veins of the immunized mice. The collected blood sample was centrifuged at 4° C. at 7,000 rpm, and a supernatant was then recovered and used as a serum sample.

4-1-4. Measurement of Antigen-Specific IgG

An ELISA plate was coated with each antigen to a final concentration of 1 μg/ml, and after completion of a reaction performed overnight, the wells were washed. In order to avoid a non-specific reaction, the wells were blocked with 1% BSA-containing PBS at 25° C. for 1 hour, and were further washed. Thereafter, serum samples were prepared by serial dilution from $2^8$, and the thus prepared serum samples were each added into the wells, followed by performing a reaction at 25° C. for 2 hours. After that, the wells were washed, HRP-labeled anti-mouse IgG was then added to the wells, followed by performing a reaction at 25° C. for 1.5 hours. After further washing, a solution of TMB (3, 3', 5, 5'-tetramethylbenzidine) as a substrate of HRP was added to the wells for color development. Immediately after termination of the reaction with 2 N sulfuric acid, the absorbance (450 nm) was measured using a microplate reader, and an antibody titer was then calculated according to an endpoint assay.

4-1. Results

Figure 4:
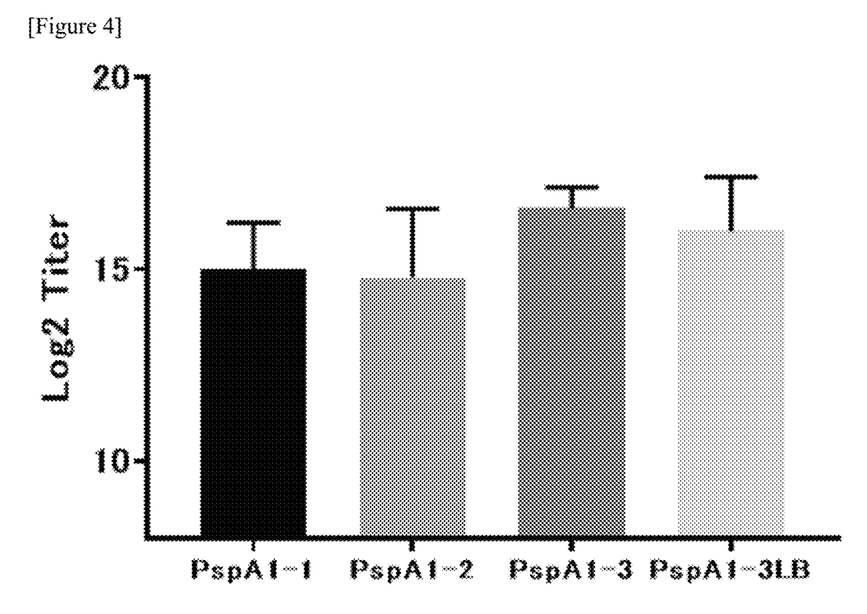
FIG. 4 shows the results obtained by comparing the effects of a nanogel nasal vaccine using PspA 1-3 LB with the effects of nanogel nasal vaccines using other PspA antigens.

It was found that, by transnasal administration of cCHP-PspA 1-1, cCHP-PspA 1-2, cCHP-PspA 1-3 or cCHP-PspA 1-3 LB to mice, IgG specific to each antigen was induced in the serum of the mice. In addition, there was no great difference among individual PspA antigens (FIG. 4).

INDUSTRIAL APPLICABILITY

The pneumococcal surface protein of the present invention and a part thereof can be used as a pneumococcal vaccine antigen. Accordingly, it is expected that the present invention will be utilized in the field of preventive medicine for infectious diseases.

---

The invention claimed is:

1. A protein comprising:
   (a) an amino acid sequence as set forth in SEQ ID NO: 3, or
   (b) an amino acid sequence having 90% or more sequence identity to SEQ ID NO: 3, wherein the aspartic acid at position 254 of SEQ ID NO: 3 is retained,
   wherein the protein has pneumococcal vaccine antigenic activity.

2. The protein according to claim 1, wherein the protein is the amino acid sequence as set forth in SEQ ID NO: 3.

3. A pneumococcal vaccine comprising:
   an adjuvant,
   a pharmaceutically acceptable carrier, and
   the protein according to claim 1.

4. A pneumococcal vaccine comprising:
   an adjuvant,
   a pharmaceutically acceptable carrier, and
   the protein according to claim 2.

5. The protein according to claim 1, wherein the protein is the amino acid sequence having 90% or more sequence identity to SEQ ID NO: 3, wherein the aspartic acid at position 254 of SEQ ID NO: 3 is retained, and wherein the protein has pneumococcal vaccine antigenic activity.

6. A pneumococcal vaccine comprising:
   an adjuvant,
   a pharmaceutically acceptable carrier, and
   the protein according to claim 5.

7. A pneumococcal vaccine comprising:
   a nanogel, and
   the protein according to claim 1.

8. A pneumococcal vaccine comprising:
   a nanogel, and
   the protein according to claim 2.

9. A pneumococcal vaccine comprising:
   a nanogel, and
   the protein according to claim 5.

* * * * *

SEQUENCE LISTING

```
<160> NUMBER OF SEQ ID NOS: 7

<210> SEQ ID NO 1
<211> LENGTH: 588
<212> TYPE: PRT
<213> ORGANISM: Streptococcus pneumoniae

<400> SEQUENCE: 1

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175
```

```
Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Lys Ala Lys Leu Ser
        210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Asn Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Lys Pro Ala Pro Ala Pro Glu Thr Pro Ala Pro Glu Ala Pro
    290                 295                 300

Ala Glu Gln Pro Lys Pro Ala Pro Ala Pro Gln Pro Ala Pro Ala Pro
305                 310                 315                 320

Lys Pro Glu Lys Pro Ala Glu Gln Pro Lys Pro Glu Lys Thr Asp Asp
                325                 330                 335

Gln Gln Ala Glu Glu Asp Tyr Ala Arg Arg Ser Glu Glu Glu Tyr Asn
            340                 345                 350

Arg Leu Thr Gln Gln Gln Pro Pro Lys Ala Glu Lys Pro Ala Pro Ala
        355                 360                 365

Pro Lys Thr Gly Trp Lys Gln Glu Asn Gly Met Trp Tyr Phe Tyr Asn
    370                 375                 380

Thr Asp Gly Ser Met Ala Thr Gly Trp Leu Gln Asn Asn Gly Ser Trp
385                 390                 395                 400

Tyr Tyr Leu Asn Ser Asn Gly Ala Met Ala Thr Gly Trp Leu Gln Tyr
                405                 410                 415

Asn Gly Ser Trp Tyr Tyr Leu Asn Ala Asn Gly Ala Met Ala Thr Gly
            420                 425                 430

Trp Ala Lys Val Asn Gly Ser Trp Tyr Tyr Leu Asn Ala Asn Gly Ala
        435                 440                 445

Met Ala Thr Gly Trp Leu Gln Tyr Asn Gly Ser Trp Tyr Tyr Leu Asn
    450                 455                 460

Ala Asn Gly Ala Met Ala Thr Gly Trp Ala Lys Val Asn Gly Ser Trp
465                 470                 475                 480

Tyr Tyr Leu Asn Ala Asn Gly Ala Met Ala Thr Gly Trp Leu Gln Tyr
                485                 490                 495

Asn Gly Ser Trp Tyr Tyr Leu Asn Ala Asn Gly Ala Met Ala Thr Gly
            500                 505                 510

Trp Ala Lys Val Asn Gly Ser Trp Tyr Tyr Leu Asn Ala Asn Gly Ala
        515                 520                 525

Met Ala Thr Gly Trp Val Lys Asp Gly Asp Thr Trp Tyr Tyr Leu Glu
    530                 535                 540

Ala Ser Gly Ala Met Lys Ala Ser Gln Trp Phe Lys Val Ser Asp Lys
545                 550                 555                 560

Trp Tyr Tyr Val Asn Gly Leu Gly Ala Leu Ala Val Asn Thr Thr Val
                565                 570                 575

Asp Gly Tyr Lys Val Asn Ala Asn Gly Glu Trp Val
            580                 585
```

<210> SEQ ID NO 2
<211> LENGTH: 588
<212> TYPE: PRT
<213> ORGANISM: Streptococcus pneumoniae

<400> SEQUENCE: 2

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asp Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Lys Pro Ala Pro Ala Pro Glu Thr Pro Ala Pro Glu Ala Pro
    290                 295                 300

Ala Glu Gln Pro Lys Pro Ala Pro Ala Pro Gln Pro Ala Pro Ala Pro
305                 310                 315                 320

Lys Pro Glu Lys Pro Ala Glu Gln Pro Lys Pro Glu Lys Thr Asp Asp
                325                 330                 335

Gln Gln Ala Glu Glu Asp Tyr Ala Arg Arg Ser Glu Glu Tyr Asn
            340                 345                 350

Arg Leu Thr Gln Gln Pro Pro Lys Ala Glu Lys Pro Ala Pro Ala
        355                 360                 365

Pro Lys Thr Gly Trp Lys Gln Glu Asn Gly Met Trp Tyr Phe Tyr Asn
    370                 375                 380
```

```
Thr Asp Gly Ser Met Ala Thr Gly Trp Leu Gln Asn Asn Gly Ser Trp
385                 390                 395                 400

Tyr Tyr Leu Asn Ser Asn Gly Ala Met Ala Thr Gly Trp Leu Gln Tyr
                405                 410                 415

Asn Gly Ser Trp Tyr Tyr Leu Asn Ala Asn Gly Ala Met Ala Thr Gly
            420                 425                 430

Trp Ala Lys Val Asn Gly Ser Trp Tyr Tyr Leu Asn Ala Asn Gly Ala
        435                 440                 445

Met Ala Thr Gly Trp Leu Gln Tyr Asn Gly Ser Trp Tyr Tyr Leu Asn
    450                 455                 460

Ala Asn Gly Ala Met Ala Thr Gly Trp Ala Lys Val Asn Gly Ser Trp
465                 470                 475                 480

Tyr Tyr Leu Asn Ala Asn Gly Ala Met Ala Thr Gly Trp Leu Gln Tyr
                485                 490                 495

Asn Gly Ser Trp Tyr Tyr Leu Asn Ala Asn Gly Ala Met Ala Thr Gly
            500                 505                 510

Trp Ala Lys Val Asn Gly Ser Trp Tyr Tyr Leu Asn Ala Asn Gly Ala
        515                 520                 525

Met Ala Thr Gly Trp Val Lys Asp Gly Asp Thr Trp Tyr Tyr Leu Glu
    530                 535                 540

Ala Ser Gly Ala Met Lys Ala Ser Gln Trp Phe Lys Val Ser Asp Lys
545                 550                 555                 560

Trp Tyr Tyr Val Asn Gly Leu Gly Ala Leu Ala Val Asn Thr Thr Val
                565                 570                 575

Asp Gly Tyr Lys Val Asn Ala Asn Gly Glu Trp Val
            580                 585

<210> SEQ ID NO 3
<211> LENGTH: 302
<212> TYPE: PRT
<213> ORGANISM: Streptococcus pneumoniae

<400> SEQUENCE: 3

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
            35                  40                  45

Asp Gln Lys Lys Thr Glu Glu Lys Ala Ala Leu Glu Lys Ala Ala Ser
        50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
                100                 105                 110

Thr Val Arg Ala Met Val Val Pro Glu Pro Glu Gln Leu Ala Glu Thr
            115                 120                 125

Lys Lys Lys Ser Glu Glu Ala Lys Gln Lys Ala Pro Glu Leu Thr Lys
        130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175
```

```
Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Ala Lys Leu Ser
210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asp Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
                275                 280                 285

Pro Glu Lys Pro Ala Pro Ala Pro Glu Thr Pro Ala Pro Glu
            290                 295                 300

<210> SEQ ID NO 4
<211> LENGTH: 302
<212> TYPE: PRT
<213> ORGANISM: Streptococcus pneumoniae

<400> SEQUENCE: 4

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
                20                  25                  30

Gln Lys Ala Leu Asp Asp Ala Lys Ala Ala Gln Lys Lys Tyr Asp Glu
            35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Ala Lys Leu Ser
210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
```

```
                        245                 250                 255
Glu Asp Tyr Phe Lys Glu Gly Leu Glu Lys Thr Ile Ala Ala Lys Lys
                260                 265                 270

Ala Glu Leu Glu Lys Thr Glu Ala Asp Leu Lys Lys Ala Val Asn Glu
            275                 280                 285

Pro Glu Lys Pro Ala Pro Ala Pro Glu Thr Pro Ala Pro Glu
        290                 295                 300

<210> SEQ ID NO 5
<211> LENGTH: 384
<212> TYPE: PRT
<213> ORGANISM: Streptococcus pneumoniae

<400> SEQUENCE: 5

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Thr Pro Ala Pro Ala Pro Ala Pro Ala Pro Ala Pro Ala Pro
    290                 295                 300

Ala Pro Ala Pro Lys Pro Ala Pro Ala Pro Lys Pro Ala Pro Ala Pro
305                 310                 315                 320
```

```
Lys Pro Ala Pro Ala Pro Lys Pro Ala Pro Ala Pro Lys Pro Ala Pro
                325                 330                 335

Ala Pro Ala Pro Ala Pro Ala Pro Lys Pro Ala Pro Ala Pro Lys Pro
            340                 345                 350

Ala Pro Ala Pro Ala Pro Ala Pro Ala Pro Ala Pro Lys Pro Glu Lys
        355                 360                 365

Pro Ala Glu Lys Pro Ala Pro Ala Pro Lys Pro Glu Thr Pro Lys Thr
370                 375                 380

<210> SEQ ID NO 6
<211> LENGTH: 356
<212> TYPE: PRT
<213> ORGANISM: Streptococcus pneumoniae

<400> SEQUENCE: 6

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Asp Tyr Ala Lys Glu Gly Phe
        195                 200                 205

Arg Ala Pro Leu Gln Ser Lys Leu Asp Ala Lys Ala Lys Leu Ser
    210                 215                 220

Lys Leu Glu Glu Leu Ser Asp Lys Ile Asp Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Pro Glu Thr Pro Ala Pro Ala Pro Ala Pro Ala Pro Ala Pro Ala Pro
    290                 295                 300

Ala Pro Ala Pro Ala Pro Ala Pro Lys Pro Ala Pro Ala Pro Lys Pro
305                 310                 315                 320
```

```
Ala Pro Ala Pro Lys Pro Ala Pro Ala Pro Ala Pro Ala Pro
                325                 330                 335

Lys Pro Glu Lys Pro Ala Glu Lys Pro Ala Pro Ala Pro Lys Pro Glu
            340                 345                 350

Thr Pro Lys Thr
        355

<210> SEQ ID NO 7
<211> LENGTH: 9
<212> TYPE: PRT
<213> ORGANISM: Streptococcus pneumoniae

<400> SEQUENCE: 7

Ala Ala Glu Glu Asn Asp Asn Val Glu
1               5
```